United States Patent
Honda et al.

(10) Patent No.: US 7,488,285 B2
(45) Date of Patent: Feb. 10, 2009

(54) SWITCH CONTROL APPARATUS FOR CONTROLLING FUNCTIONS OF A SWITCH BY DISPLAYING INFORMATION RELATING TO THE SWITCH CONTROLLING A PLURALITY OF MEDICAL DEVICES

(75) Inventors: Yoshitaka Honda, Hachioji (JP); Kazue Tanaka, Sagamihara (JP); Hiroo Ono, Koganei (JP)

(73) Assignee: Olympus Corporation, Tokyo (JP)

( * ) Notice: Subject to any disclaimer, the term of this patent is extended or adjusted under 35 U.S.C. 154(b) by 382 days.

(21) Appl. No.: 10/925,109

(22) Filed: Aug. 24, 2004

(65) Prior Publication Data
US 2005/0049458 A1      Mar. 3, 2005

(30) Foreign Application Priority Data
Aug. 28, 2003   (JP) .............................. 2003-305574

(51) Int. Cl.
*A61B 1/00* (2006.01)
*A61B 1/04* (2006.01)
(52) U.S. Cl. ..................................... 600/126; 600/118
(58) Field of Classification Search ................. 600/101, 600/117, 118, 132
See application file for complete search history.

(56) References Cited

U.S. PATENT DOCUMENTS 4,854,301 A * 8/1989 Nakajima ................... 600/102
5,259,365 A * 11/1993 Nishikori et al. ............ 600/102
5,627,584 A * 5/1997 Nishikori et al. ............ 348/72
5,877,802 A * 3/1999 Takahashi et al. ............ 348/71
7,097,640 B2 * 8/2006 Wang et al. ................... 606/10
2002/0115917 A1   8/2002 Honda et al.

FOREIGN PATENT DOCUMENTS

| JP | 09-325091 | 12/1997 |
| JP | 11-318916 | 11/1999 |
| JP | 2001-314411 | 11/2001 |
| JP | 2002-058641 | 2/2002 |
| JP | 2002-306504 | 10/2002 |

* cited by examiner

*Primary Examiner*—Linda C Dvorak
*Assistant Examiner*—Philip R Smith
(74) *Attorney, Agent, or Firm*—Scully, Scott, Murphy & Presser P.C.

(57) ABSTRACT

An image signal captured by a camera head and outputted from an image processor is inputted into a foot switch control device. The image signal is processed in a display control unit of the foot switch control device, inputted into a display and displayed thereon. The display control unit reads out an image indicating the foot switch state corresponding to the foot switch function that is presently allocated to the inputted endoscopic image from a memory unit and superimposes this image on the endoscopic image.

13 Claims, 19 Drawing Sheets

FIG.13
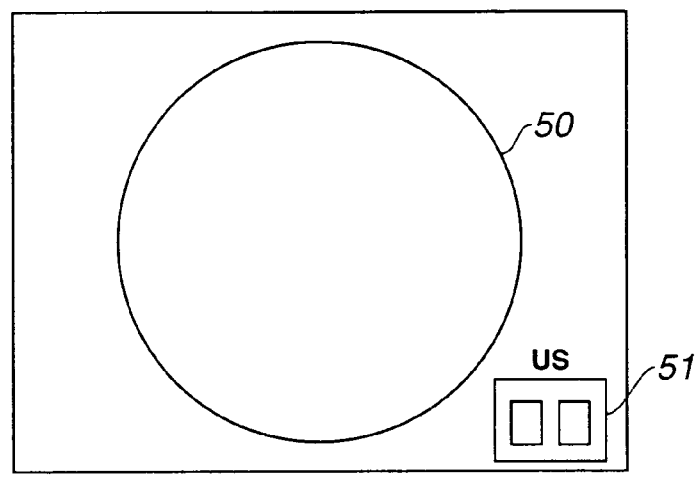
↓ CHANGING-OVER WITH SELECTION SWITCH
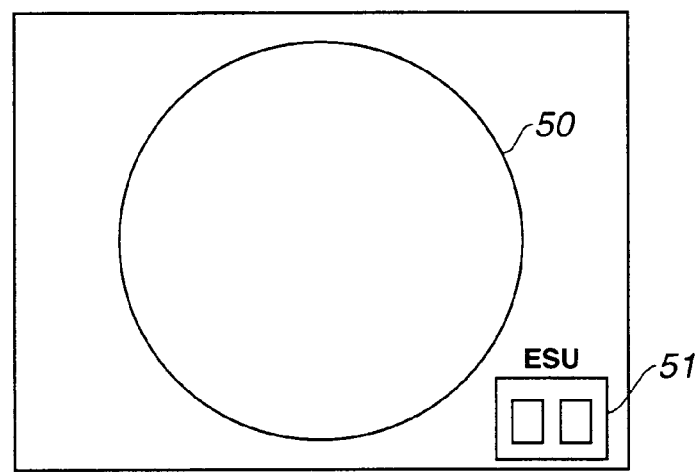
↓ AUTOMATIC CHANGING-OVER AFTER 10 sec
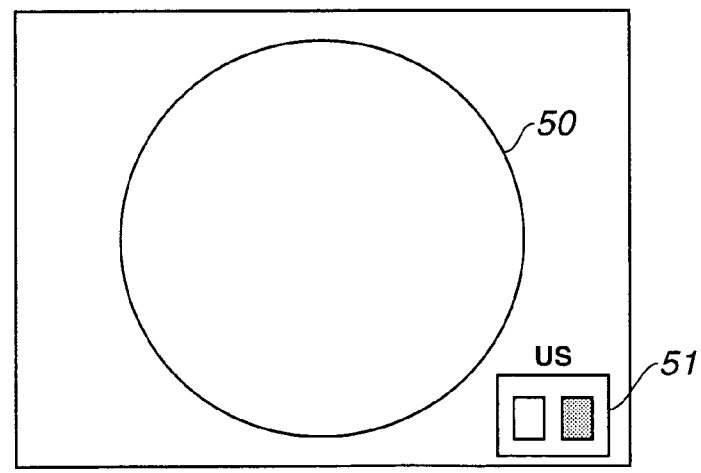

SWITCH CONTROL APPARATUS FOR CONTROLLING FUNCTIONS OF A SWITCH BY DISPLAYING INFORMATION RELATING TO THE SWITCH CONTROLLING A PLURALITY OF MEDICAL DEVICES

This application claims benefit of Japanese Application No. 2003-305574 filed in Japan on Aug. 28, 2003, the contents of which are incorporated by this reference.

BACKGROUND OF THE INVENTION

1. Field of the Invention

The present invention relates to a switch control apparatus for controlling the functions of a switch which controls a plurality of medical devices.

2. Description of the Related Art

As disclosed, for example, in Japanese Patent Application Laid-open No. 2002-306504, a surgical system is known in which a plurality of surgical devices can be operated by using one foot switch. Furthermore, a surgical system is also known in which the surgical system comprises display means for superimposing the switch functions allocated to each functional pedal of the foot switch on an endoscopic image, as has been disclosed in Japanese Patent Application Laid-open No. 11-318916.

As example of the surgical system is shown in FIG. 20. A surgical system 101 comprises a display 102, an image processor 103, a camera head 104, a light source 105, an ultrasonic surgical device 106, an electric scalpel 107, a foot switch control device 108, and a foot switch 109. Further, the foot switch 109, as shown in FIG. 21, comprises a first functional switch 109a, a second functional switch 109b, and a selection switch 109c.

A foot switch signal of the foot switch 109 for controlling the ultrasonic surgical device 106 and electric scalpel 107 is transmitted via a foot switch signal control unit 108b. The mode of the foot switch signal control unit 108b is switched according to the output device settings that are set by the selection switch 109c of the foot switch 109 shown in FIG. 21 or by another selection switch which is not shown in the figures, and the push-down signal of each pedal of the foot switch 109 is outputted to a device corresponding to the signal indicating either a maximum output or a set output of the ultrasonic surgical device 106, a monopolar or bipolar mode, and a section or coagulation of the electric scalpel 107.

The image signal outputted by the image processor 103 is inputted into the display 102 via the display control unit 108a of the foot switch control device 108 and an endoscopic image is displayed. The display control unit 108a superimposes a foot switch state display image indicating the state of the foot switch 109 on the inputted endoscopic image. The foot switch state display image is located, for example, in the right corner of the screen and, as shown in FIG. 22 and FIG. 23, represents the arrangement of foot switches, functions corresponding to each pedal, and an ON/OFF state of each pedal. When the foot switch is OFF, as shown in FIG. 22, the foot switch pedal is displayed as a rectangular that has not been painted over, and when the foot switch is ON, as shown in FIG. 23, the rectangular showing the pedal is displayed as being painted over with the prescribed color. Furthermore, the display of the foot switch state can be also implemented by inverting and inverting back the switch image displayed by the prescribed color.

If a foot switch state display image is displayed during surgery, it could sometimes impede the observation of the endoscopic image. Therefore, it is also possible not to display the foot switch state display image. In this case, the functions allocated to each pedal of the foot switch can be recognized by displaying the panel provided in the foot switch control device 108.

Furthermore, for example, as disclosed in Japanese Patent Application laid-open No. 2001-314411, a surgical device is also known in which two or more foot switches are connected to one or a plurality of surgical devices and the device can be operated by any foot switch.

SUMMARY OF THE INVENTION

The switch control apparatus in accordance with the present invention comprises:

an image reception unit for receiving an image signal from an image pickup device for picking up the image of an object;

a medical instrument;

an operation switch for operating the medical instrument;

a selection switch for changing the allocation state of the medical instrument and the operation switch;

a changing-over signal reception unit for receiving a changing-over signal from the selection switch;

an image synthesis unit for superimposing the information relating to the selection switch based on the changing-over signal received by the changing-over signal reception unit and the object image based on the image signal and synthesizing an image signal for displaying in the image reception unit; and a display switching unit for switching between the display and no-display modes of the information relating to the operation switch displayed in the display reception unit.

Other features and advantages of the present invention will hereinafter become more fully apparent from the following description.

BRIEF DESCRIPTION OF THE DRAWINGS

FIG. 1 is a structural diagram illustrating the structure of a medical system;

FIG. 2 is a structural diagram illustrating the structure of the foot switch shown in FIG. 1;

FIG. 3 is a first figure illustrating the image displayed on the display shown in FIG. 1;

FIG. 4 is a second figure illustrating the image displayed on the display shown in FIG. 1;

FIG. 5 is a first flowchart for explaining the operation of the foot switch control device shown in FIG. 1;

FIG. 6 illustrates the processing shown in FIG. 5;

FIG. 7 is a second flowchart for explaining the operation of the foot switch control device shown in FIG. 1;

FIG. 8 is a third figure illustrating the image displayed on the display shown in FIG. 1;

FIG. 9 is a third flowchart for explaining the operation of the foot switch control device shown in FIG. 1;

FIG. 10 is a fourth flowchart for explaining the operation of the foot switch control device shown in FIG. 1;

FIG. 11 to FIG. 13 relate to Embodiment 2 of the present invention;

FIG. 11 is a structural diagram illustrating the structure of a medical system;

FIG. 12 is a flowchart for explaining the operation of the foot switch control device shown in FIG. 11;

FIG. 13 is a figure illustrating the image displayed at the display shown in FIG. 11;

FIG. 15 is a structural diagram illustrating the structure of a medical system;

FIG. 16 is a flowchart for explaining the operation of the foot switch control device shown in FIG. 15;

FIG. 17 is a first figure illustrating an image displayed on the display shown in FIG. 15;

FIG. 18 is a second figure illustrating an image displayed on the display shown in FIG. 15;

FIG. 19 is a third figure illustrating an image displayed on the display shown in FIG. 15;

FIG. 20 is a structural diagram illustrating the structure of the conventional surgical system.

FIG. 21 is a structural diagram illustrating the structure of the foot switch shown in FIG. 20;

FIG. 22 is a first figure illustrating the image displayed on the display shown in FIG. 20; and FIG. 23 is a second figure illustrating the image displayed on the display shown in FIG. 20.

DETAILED DESCRIPTION OF THE PREFERRED EMBODIMENTS

Embodiment 1

Figure 1:
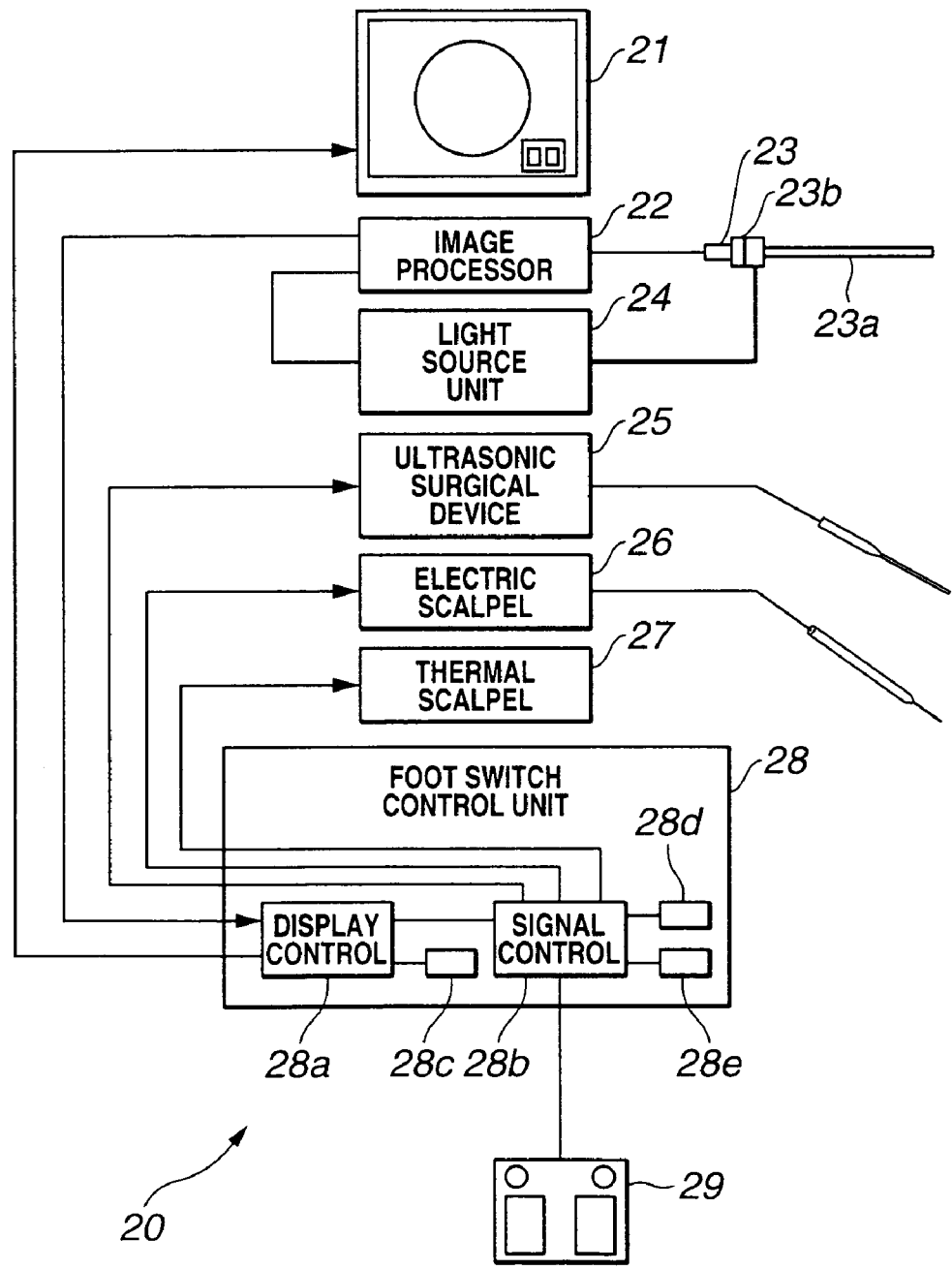
FIG. 1 to FIG. 10 relate to Embodiment 1 of the present invention.

As shown in FIG. 1, a medical system 20 of the present embodiment comprises a display 21, an image processor 22, a camera head 23, a light source device 24, and ultrasonic surgical device 25, an electric scalpel 26, a thermal scalpel 27, a foot switch control device 28, and a foot switch 29. The light source device 24 supplies illumination light to an endoscope 23a. The camera head 23 is freely detachably connected to an ocular 23b of the endoscope 23a, picks up an endoscopic image and outputs the picked-up signal to an image processor 22.

The image signal received from the camera head 23 and outputted from the image processor 22 is inputted into the foot switch control device 28. The image signal is then processed in a display control unit 28a of the foot switch control device 28, inputted into the display 21, and displayed. The display control unit 28a reads an image indicating the foot switch state corresponding to a foot switch function that is presently allocated to the inputted endoscopic image and superimposes this image on the endoscopic image.

Figure 2:
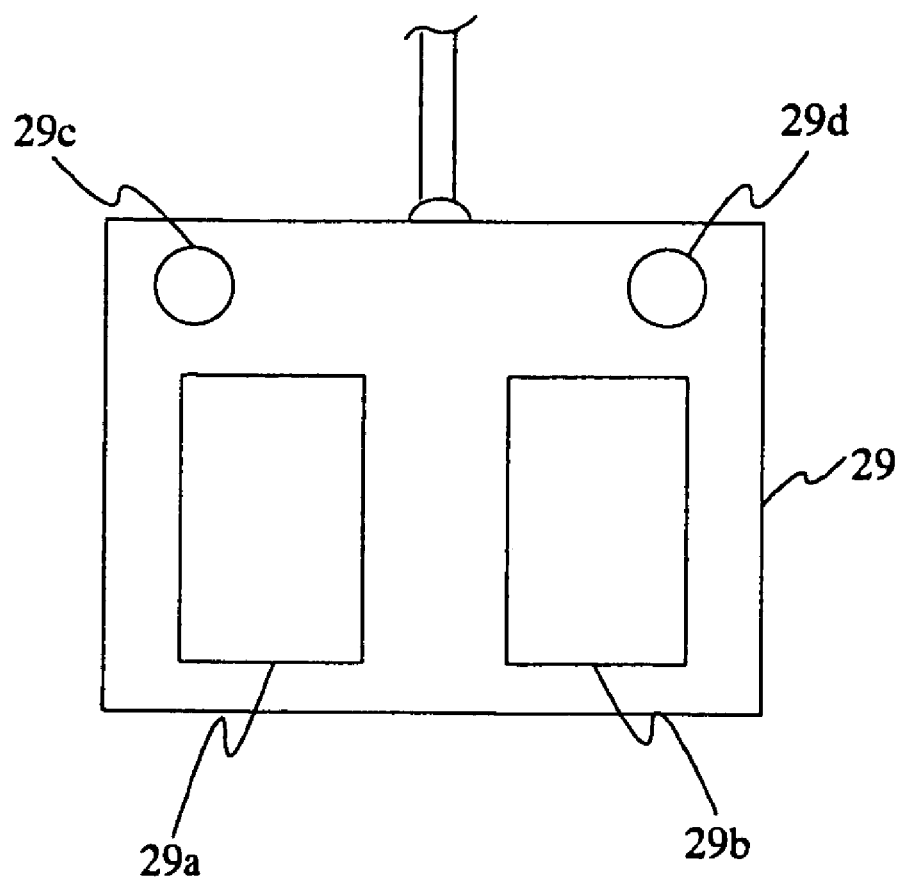

As shown in FIG. 2, the foot switch 29 comprises a first functional switch 29a, a second functional switch 29b, a selection switch 29c, and a foot switch state display toggle switch 29d.

Figure 3:
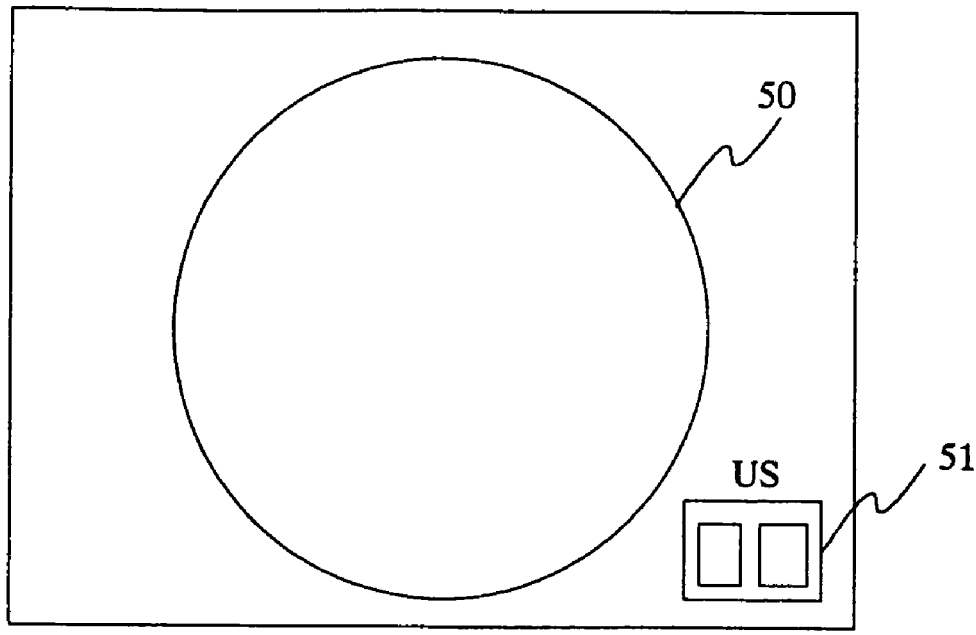
Figure 4:
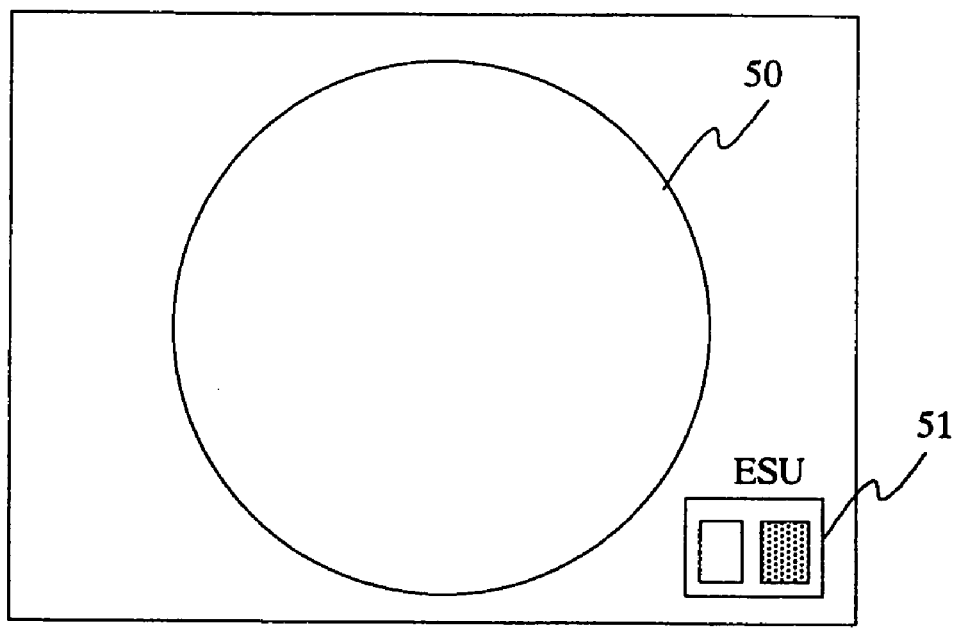

FIG. 3 and FIG. 4 show the superposition of the foot switch state display image 51, which indicates the state of the foot switch, on the lower right corner of the endoscopic image 50. The presently allocated function is indicated by displaying above the foot switch state display image 51 or on a pedal (for example, "ESU" indicating an electric scalpel or "US" indicating an ultrasonic surgical unit).

When a functional switch of the foot switch 29 is ON, for example, if the second functional switch 29b is ON, the foot switch state display image 51 corresponding to the second functional switch 29b is changed to a display indicating the foot switch signal ON, as shown in FIG. 4 (the rectangle may be painted over or color thereof may be inverted).

Figure 5:
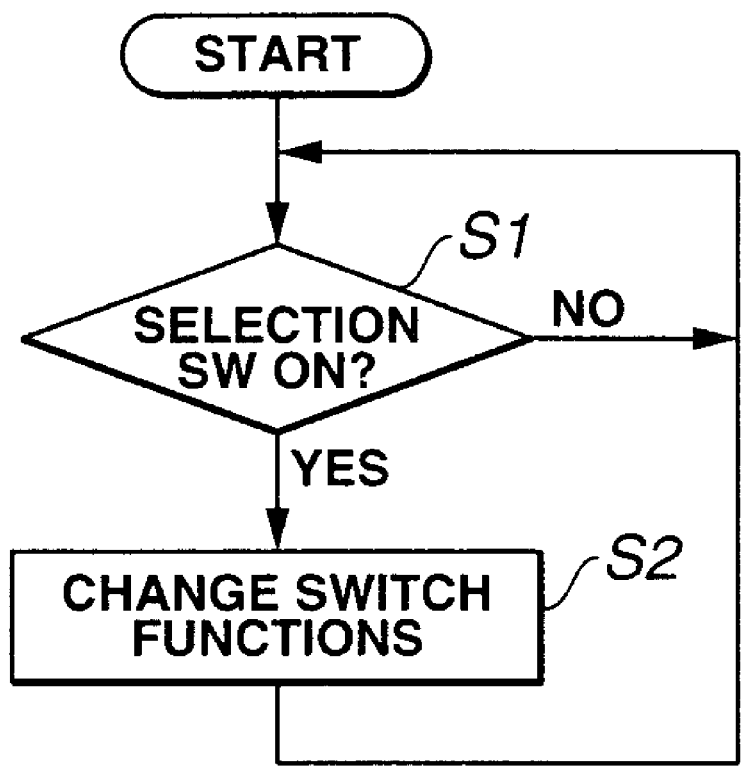
Figure 6:
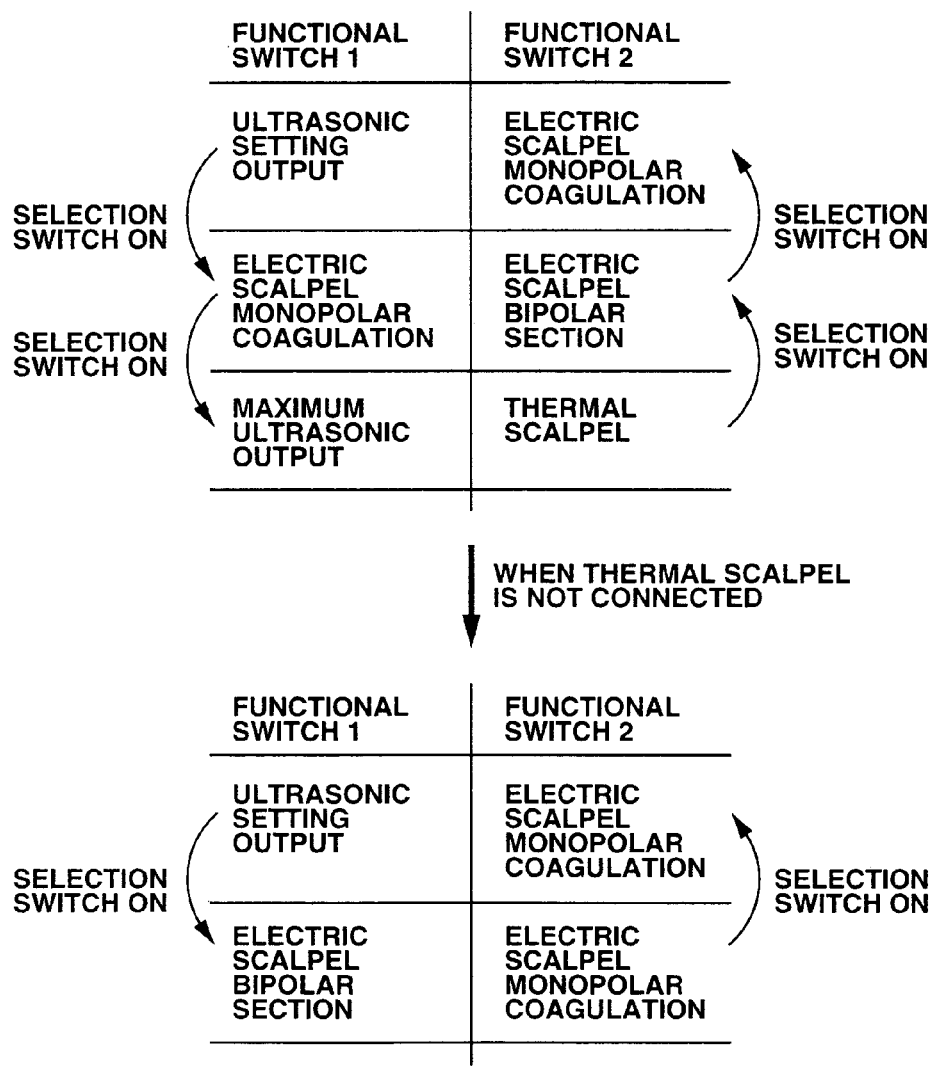

Further, according to a flow chart shown in FIG. 5, if the foot switch signal control unit 28b of the foot switch control device 28 detects that the surgeon has pushed the selection switch 29c of the foot switch 29 (step S1), then the function allocated to each pedal of the foot switch 29 is changed to a combination stored in a memory unit 28e, as shown in FIG. 6, each time the selection switch 29c is pushed (step S2).

At this time, the foot switch signal control unit 28b changes the signal connection in order to determine as to, to which one, the ultrasonic surgical device 25, electric scalpel 26, and thermal scalpel 27, the ON/OFF signal of the functional switches 29a, 29b of the foot switch should be outputted, and also notifies the display control unit 28a about the newly selected state. The display control unit 28a generates the foot switch state display image 51 that will be superimposed following the foots switch state display that is stored in the memory unit 28d and changes a display corresponding to a new foot switch function.

Figure 7:
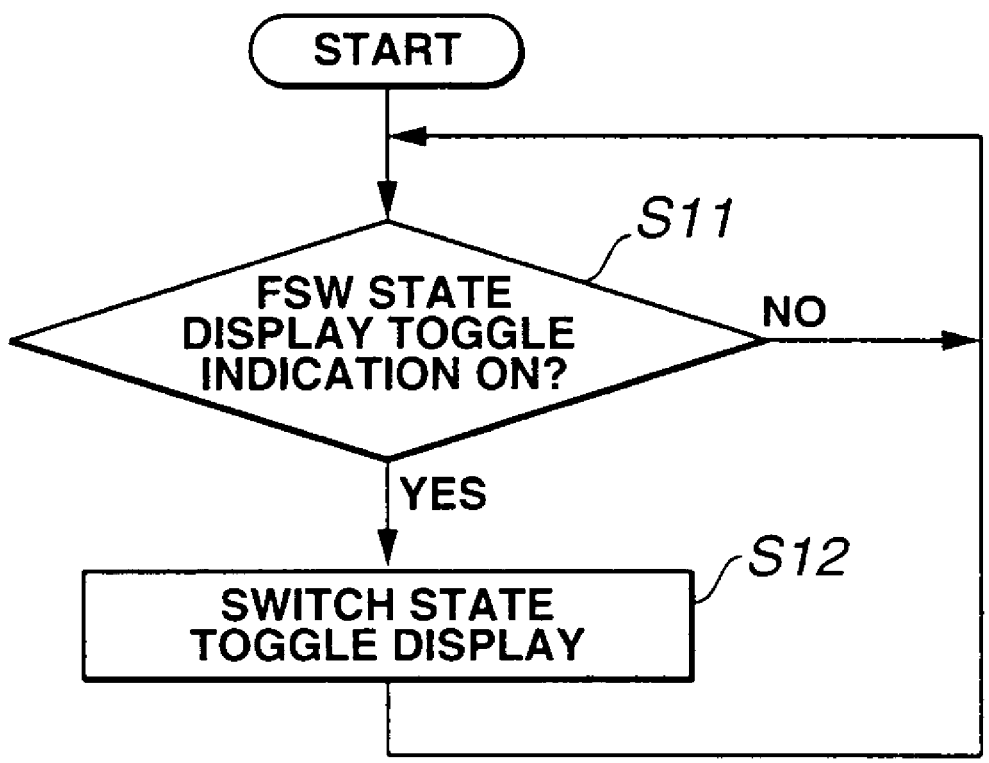

Furthermore, in the medical system control device 1 of the first embodiment, the user can easily change a display mode (display or no display) of the foot switch state display image according to the flow chart shown in FIG. 7. For example, if the foot switch state display toggle switch 29d is pushed (step S11) after the foot switch state display image 51 has been superimposed, the foot switch state display is turned OFF (step S12) and, as shown in FIG. 8, a state is assumed in which the foot switch state display image 51 is not superimposed on the endoscopic image 50.

Figure 8:
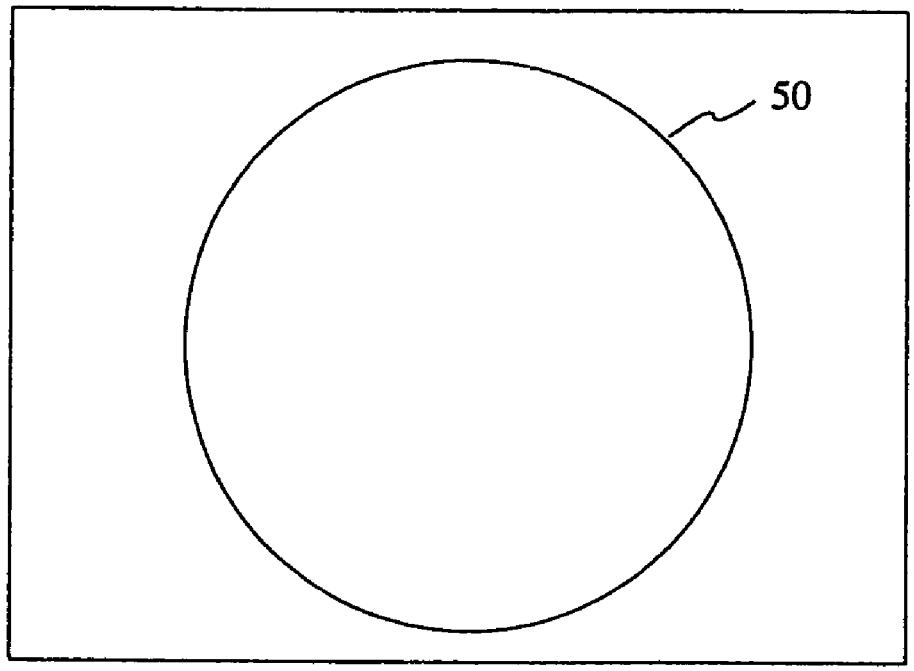

Thus, if the foot switch control unit 28b detects that the foot switch state display toggle switch 29d of the foot switch 29 shown in FIG. 6 or at the front panel of the foot switch control device 28 is pushed when the foot switch state display is ON and sends a foot switch state display changing-over signal to the display control unit 28a, the display control unit 28a turns the switch state display OFF, as shown in FIG. 8.

If there is a notification that the foot switch state display toggle switch 29d has been pushed again, the foot switch state display is turned OFF, as shown in FIG. 3. Furthermore, if the first functional switch 29a or second functional switch 29b of the foot switch is stepped on when the foot switch state display is ON, as shown in FIG. 4, the display of the functional switch icon corresponding to the foot switch state display is changed to the display (inversion, painting over or the like) indicating the functional switch ON.

Figure 9:
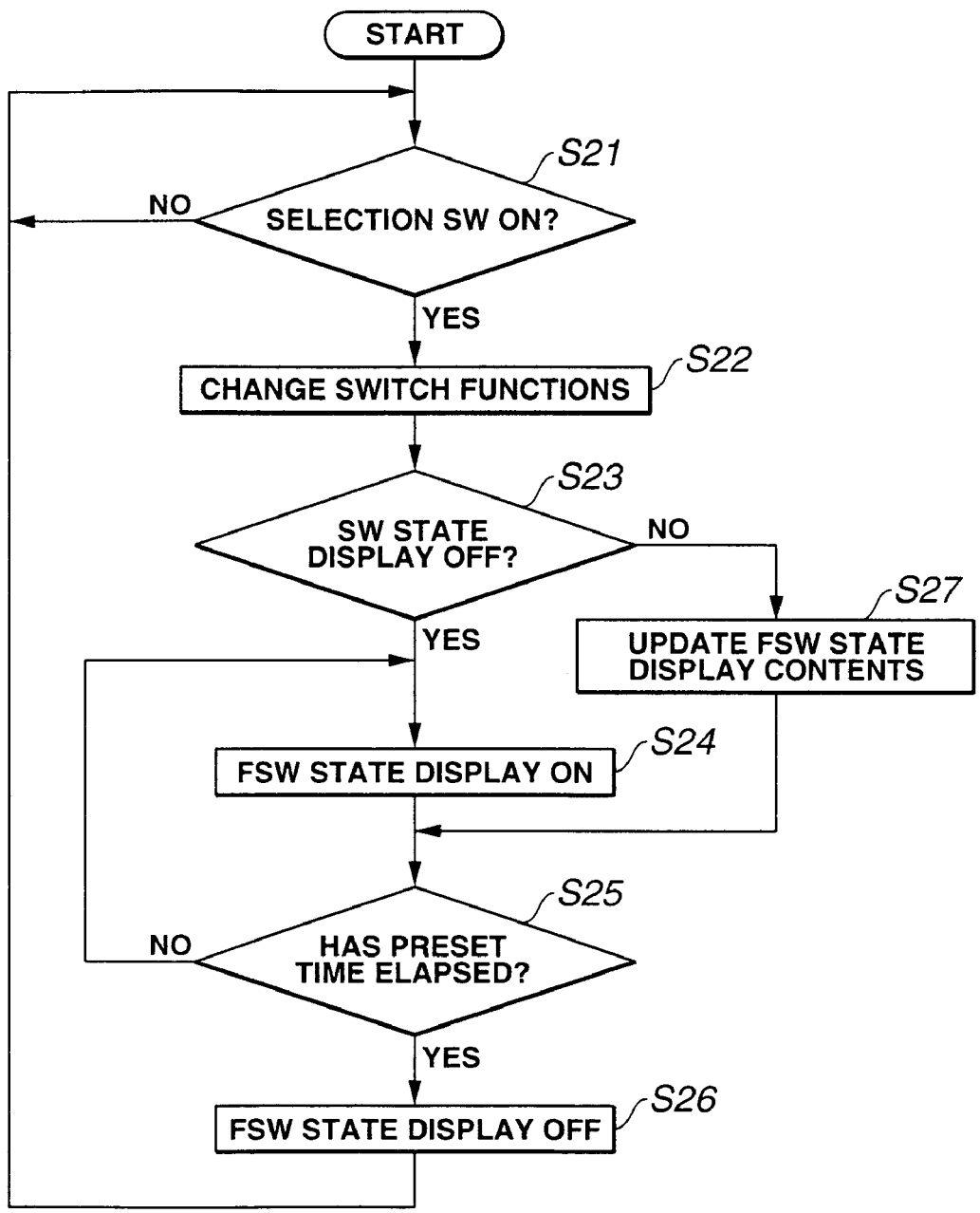

In this case, if the foot switch function is changed when the foot switch state display is OFF, the user cannot recognize the newly allocated function. For this reason, when either the first functional switch 29a or the second functional switch 29b of the foot switch 29 is stepped on, the foot switch state display is temporarily turned ON according to the flow of FIG. 9.

Thus, if the foot switch control unit 28b detects that the selection switch 29c has been pushed (step S21), it changes the foot switch function (step S22). When the present foot switch state display is OFF (step S23), the display control unit 28a is notified and the foot switch state display is turned ON (step S24). Further, after the prescribed time has elapsed (step S25), the foot switch control unit 28b transmits a command to turn OFF the foot switch state display to the display control unit 28a (step S26). When the present foot switch state display is ON (step S23), the FSW state display contents are updated and displayed (step S27) and the program thereafter proceeds to step S25.

When the functional switch is changed by the selection switch 29c, the switch state is displayed (when the display function is OFF, it is changed to ON and displayed). Then, after a prescribed time elapses, the switch display state is switched OFF. When either the first functional switch 29a or the second functional switch 29b is stepped on after a prescribed time has elapsed since the function was changed by the selection switch 29c, the switch state is displayed without executing the function allocated to the functional switch and the function allocated to the functional switch is executed at a stage where the next functional switch is stepped on.

Figure 10:
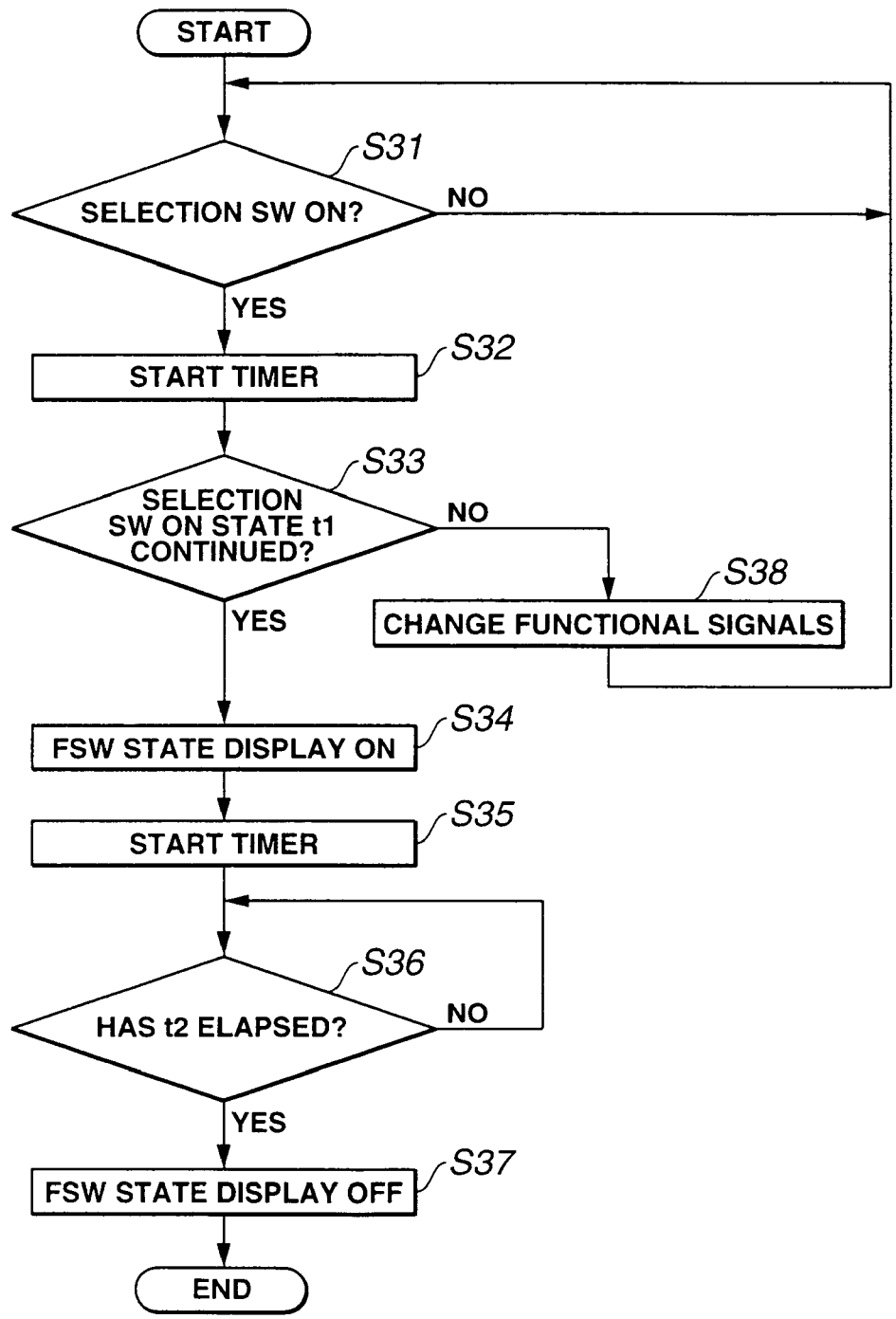
Figure 21:
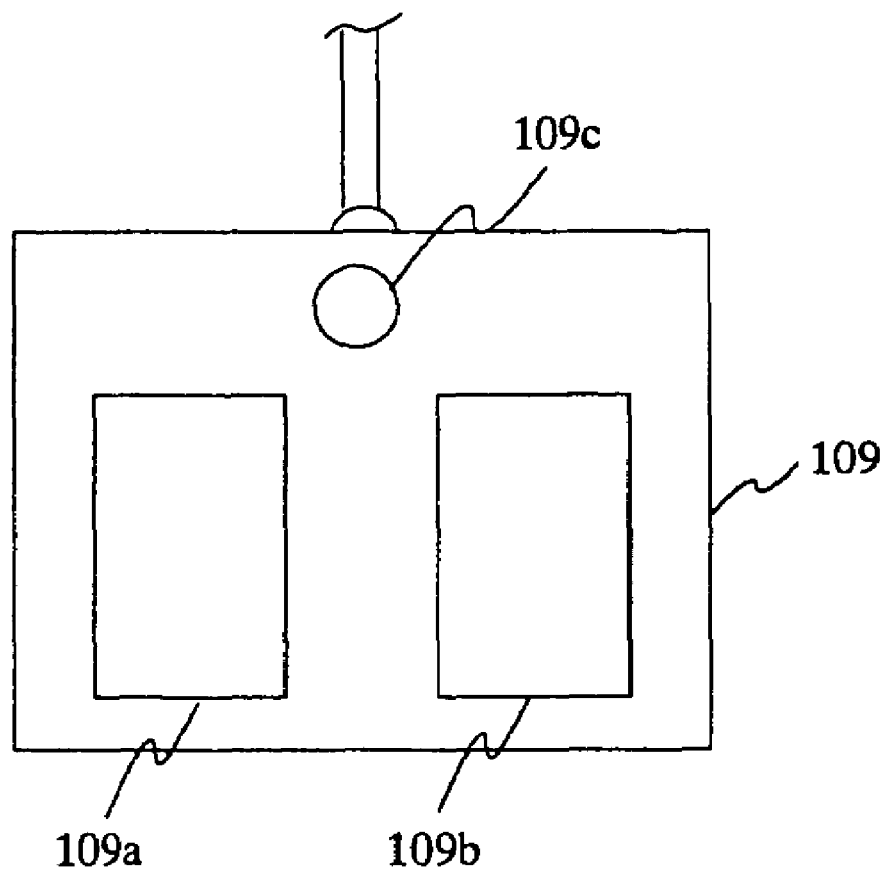
Figure 22:
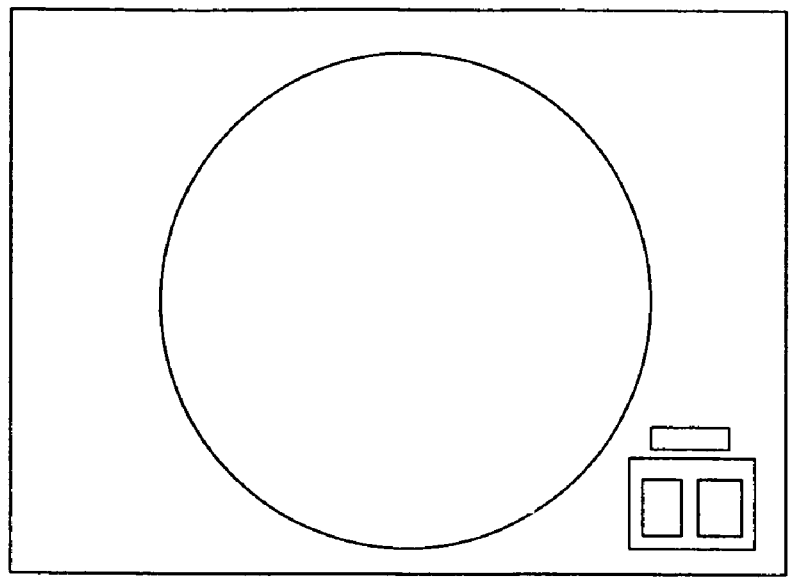
Figure 23:
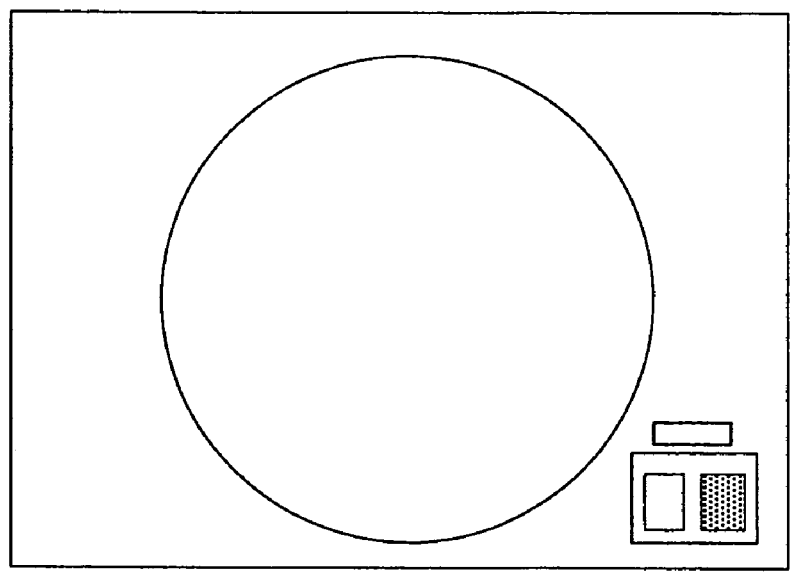

Further, the foot switch state display can be also changed in the same manner when a foot switch 109 (shown in FIG. 21) that has been conventionally employed is used. The relevant flow is shown in FIG. 10.

Thus, if the selection switch 109c of the foot switch 109 is detected to be pushed (step S31), the foot switch control unit 28b starts counting by using a timer (step S32). When the selection switch 109c is continuously pushed till the prescribed time t1 elapses (step S33), the foot switch state display is changed within the prescribed time t2 (steps S34-S37). When the selection switch 109c was released before the prescribed time t1 has elapsed, the functions that are allocated to each pedal of the foot switch 109 are changed as shown in FIG. 6 (step S38).

Further, the functions allocated to each functional switch of the foot switch 29 and the changing sequence thereof are not limited to the combination shown in FIG. 6. Furthermore, if a device connected to the foot switch control device 28 has been detected and the corresponding apparatus has not been connected, it is also possible that the combination of corresponding foot switch functions be not allocated. Moreover, the user can also define in advance at least one combination of foot switch functions that will be allocated to each functional pedal of the foot, record it in the foot switch control device 28, and use.

With the present embodiment, the foot switch state display can be appropriately ON/OFF switched and used. Furthermore, because the functions that are allocated to the foot switch can be recognized at all times, it is not difficult to understand the allocation of foot switch functions even when the state display at the foot switch is OFF.

Embodiment 2

Because Embodiment 2 is almost identical to Embodiment 1, only the difference therebetween will be explained, identical components will be assigned with the same reference symbols, and the explanation thereof will be omitted.

Figure 11:
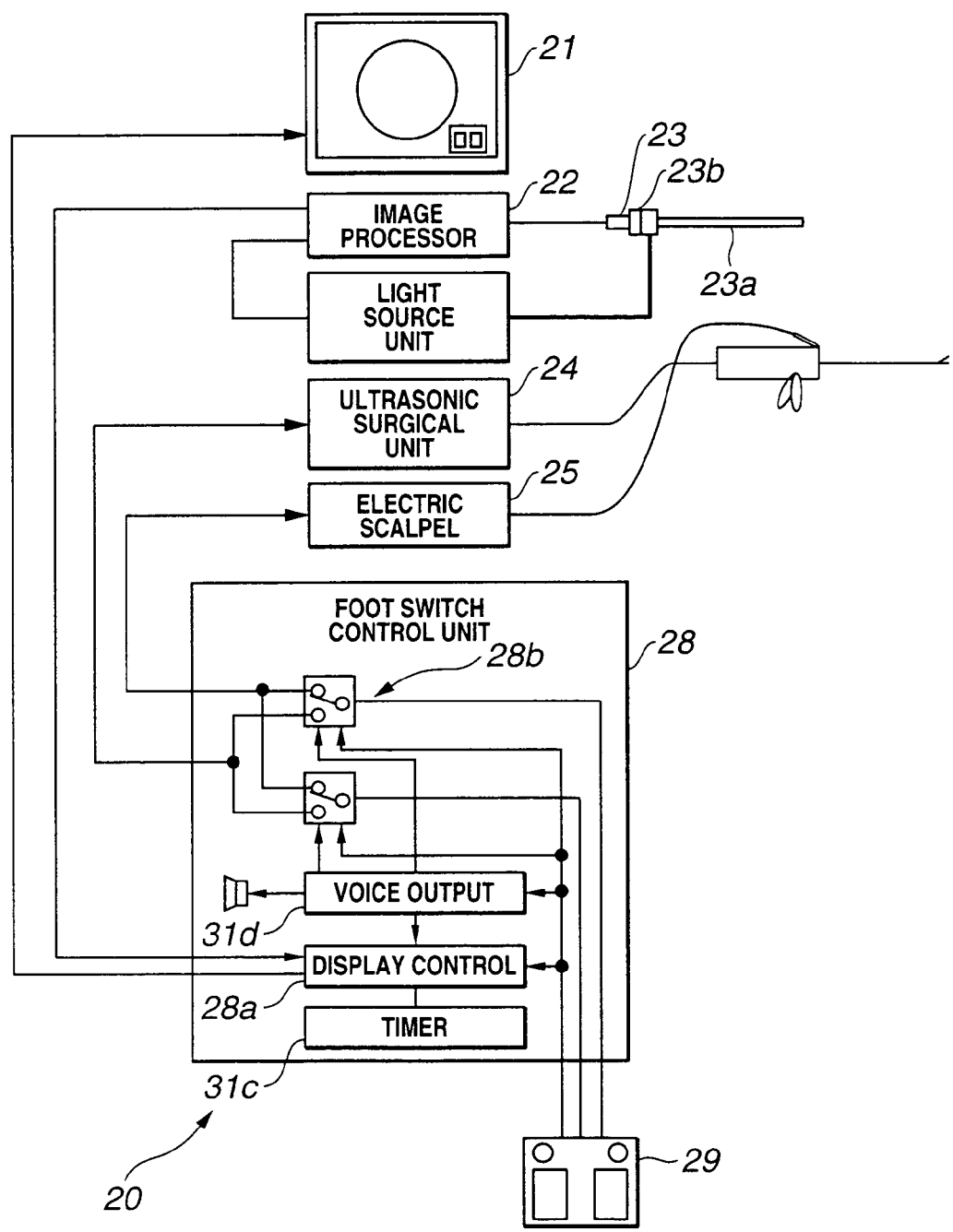

As shown in FIG. 11, a foot switch control device 28 of the present embodiment has a timer 31c and a voice output unit 31d in addition to a display control unit 28a, and a foot switch signal control unit 28b.

Figure 12:
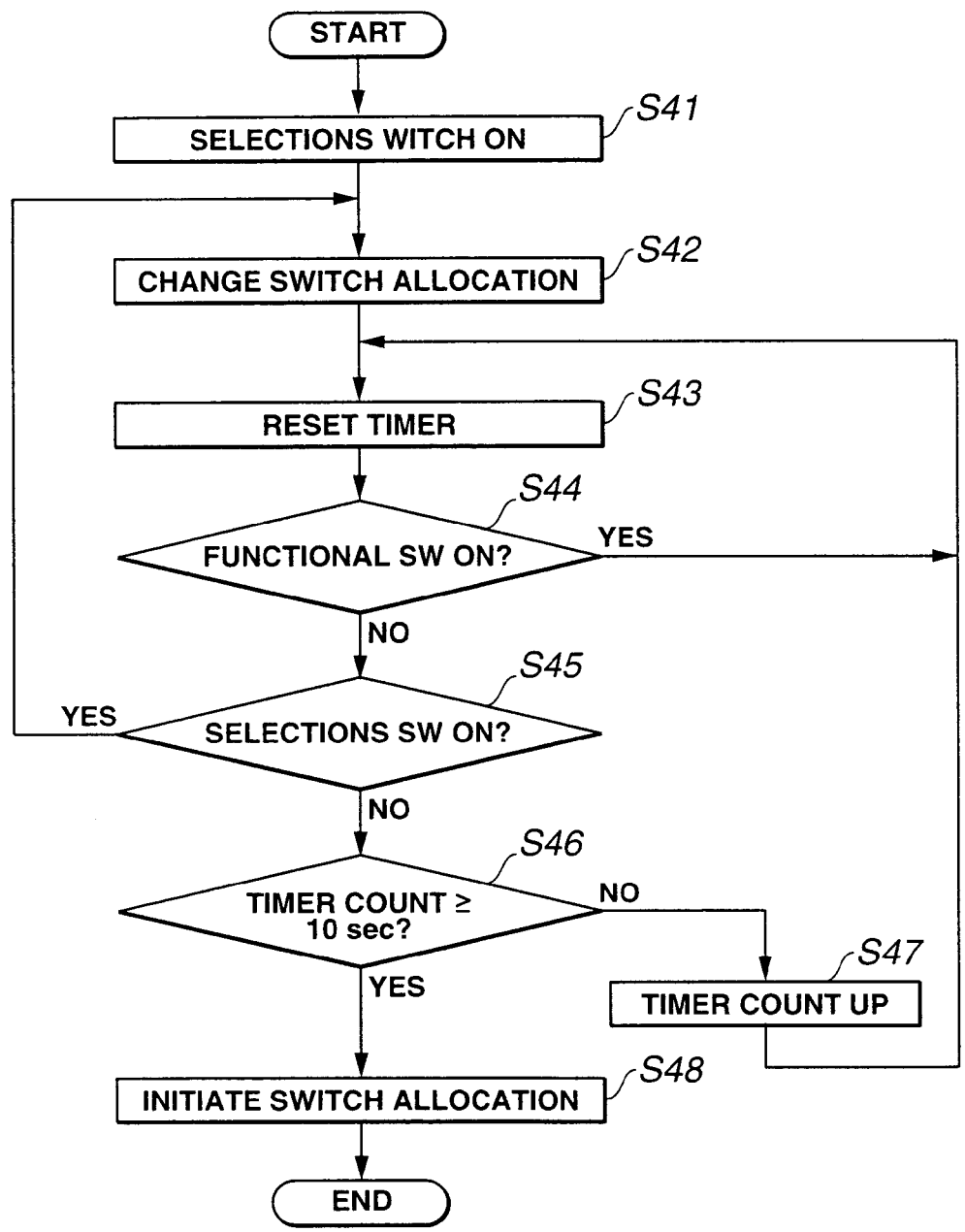

As shown in FIG. 12, if the selection switch 29c of the foot switch 29 is stepped on (step S41), the foot switch control device 28 changes the allocation of foot switch functions (step S42), the foot switch state display image 51 which is outputted by the display control unit 28a changes, a signal is inputted into the timer 31c, and count is initiated.

Further, if there is an input of the first functional switch 29a or 29b of the foot switch 29 before the prescribed time, for example, 10 sec, elapses, then the timer 31c is reset (steps S43-S47). If the prescribed time, for example, 10 sec, elapses without the timer 31c being reset, as shown in FIG. 13, a time excess signal is outputted from the timer 31c to the foot switch signal control unit 28b and the allocation of foot switch functions and foot switch state display are changed to the initial state (step S48).

When the foot switch state display becomes OFF after the prescribed time, for example, 10 sec, has passed and the allocation of foot switch functions is changed, the fact that the allocation of foot switch functions is changed can be conveyed to the user by switching the switch state display ON for the prescribed time and then again switching it OFF, in the same manner as in Embodiment 1. In the same case, the fact that the allocation of foot switch functions is changed may be also conveyed to the user by outputting a voice signal from the voice output unit 31d.

In accordance with the present invention, the allocation of foot switch functions is returned to the initial state if the functions have not been used within a certain interval. Therefore, the user does not have to decide to which state the functions are changed, and the operations can be easily understood.

Embodiment 3

Embodiment 3 is almost identical to Embodiment 2. Therefore, only the difference therebetween will be explained. The identical components are assigned with the same reference symbols and the explanation thereof is herein omitted.

Figure 14:
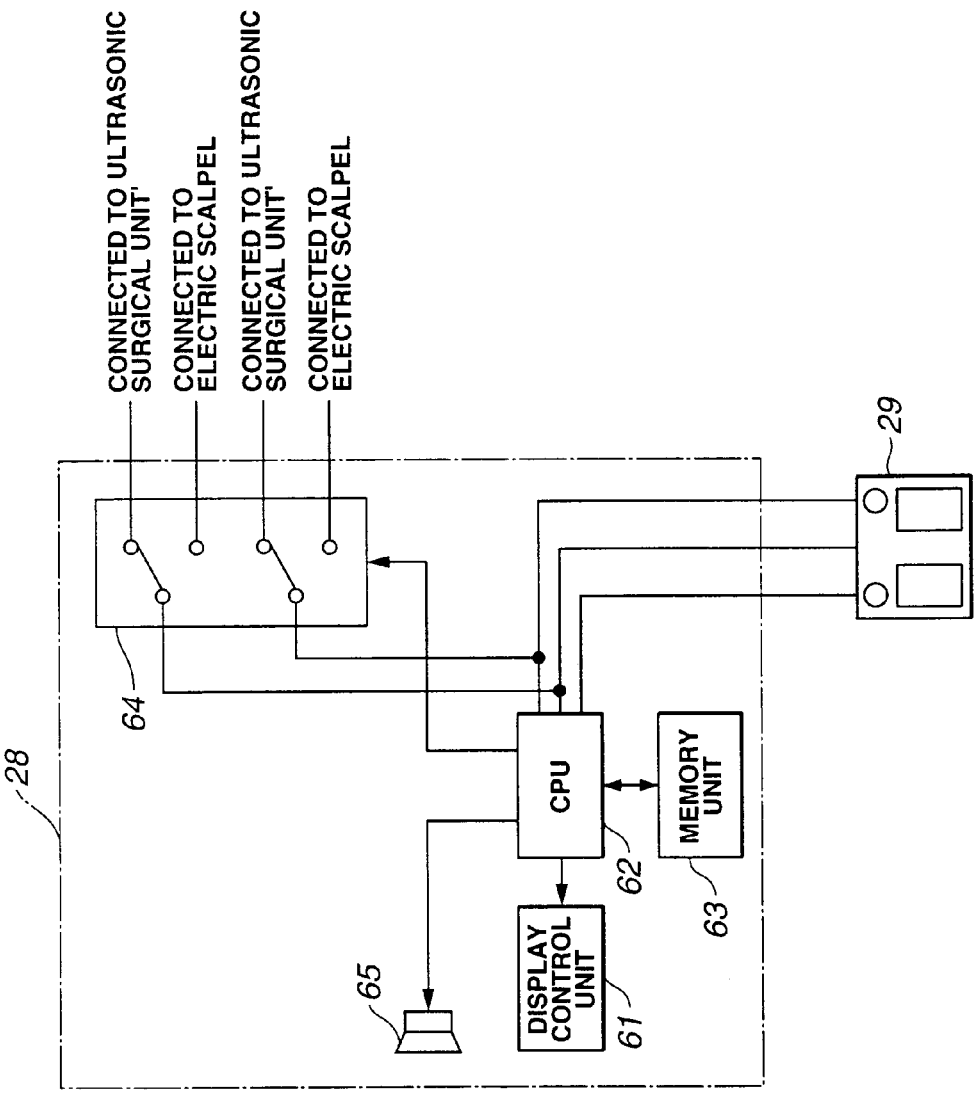
FIG. 14 is a structural diagram illustrating the structure of a foot switch control device of Embodiment 3 of the present invention.

As shown in FIG. 14, the foot switch control device 28 of the present embodiment comprises a display control unit 61, a CPU 62, a memory unit 63, a changing-over unit 64, and a voice output unit 65.

If the functional switches 29a, 29b of the foot switch 29 are stepped on, a functional switch signal is inputted into the CPU 62 and changing-over unit 64 and outputted to an ultrasonic surgical device 25 or electric scalpel 26, which is connected to the foot switch control device 28 according to the foot switch function allocation at this point of time.

Furthermore, if the selection switches 29c of the foot switch 29 are stepped on, the CPU 62 detects the selection switch signal, controls the change unit 64 according to the foot switch function allocation table stored in the memory unit 63, and changes the allocation of the functions to each functional switch 29a, 29b of the foot switch 29. Furthermore, the foot switch function signal indicating that the allocation of foot switch functions is changed is outputted to the display control unit 61 and the foot switch state display is changed. It is also possible to output a voice output command signal to the voice output unit 65 and notify the user with the voice output that the allocation of foot switch functions is changed.

Further, if the selection switch signal is detected, the CPU 62 initializes the timer variable and conducts counting for each fixed interval. When the selection switch signal or functional switch signal has been inputted before the prescribed count is reached, the timer variable is initialized and the count is started again. If the prescribed count is reached without the selection switch signal or functional switch signal being inputted, the CPU 62 controls the changing-over unit 64 to set the allocation of foot switch functions to the initial state that is set by memory means 63 and outputs a foot switch function signal to the display control unit 61. At this time, it is also possible to output a voice output command signal to the voice output unit 65 and notify the user with the voice output that the allocation of foot switch functions is changed.

With this embodiment, the effect identical to that obtained in Embodiment 2 can be realized with a software.

Embodiment 4

Embodiment 4 is almost identical to Embodiments 1 and 2. Therefore, only the difference therebetween will be explained. The identical components are assigned with the same reference symbols and the explanation thereof is herein omitted.

Figure 15:
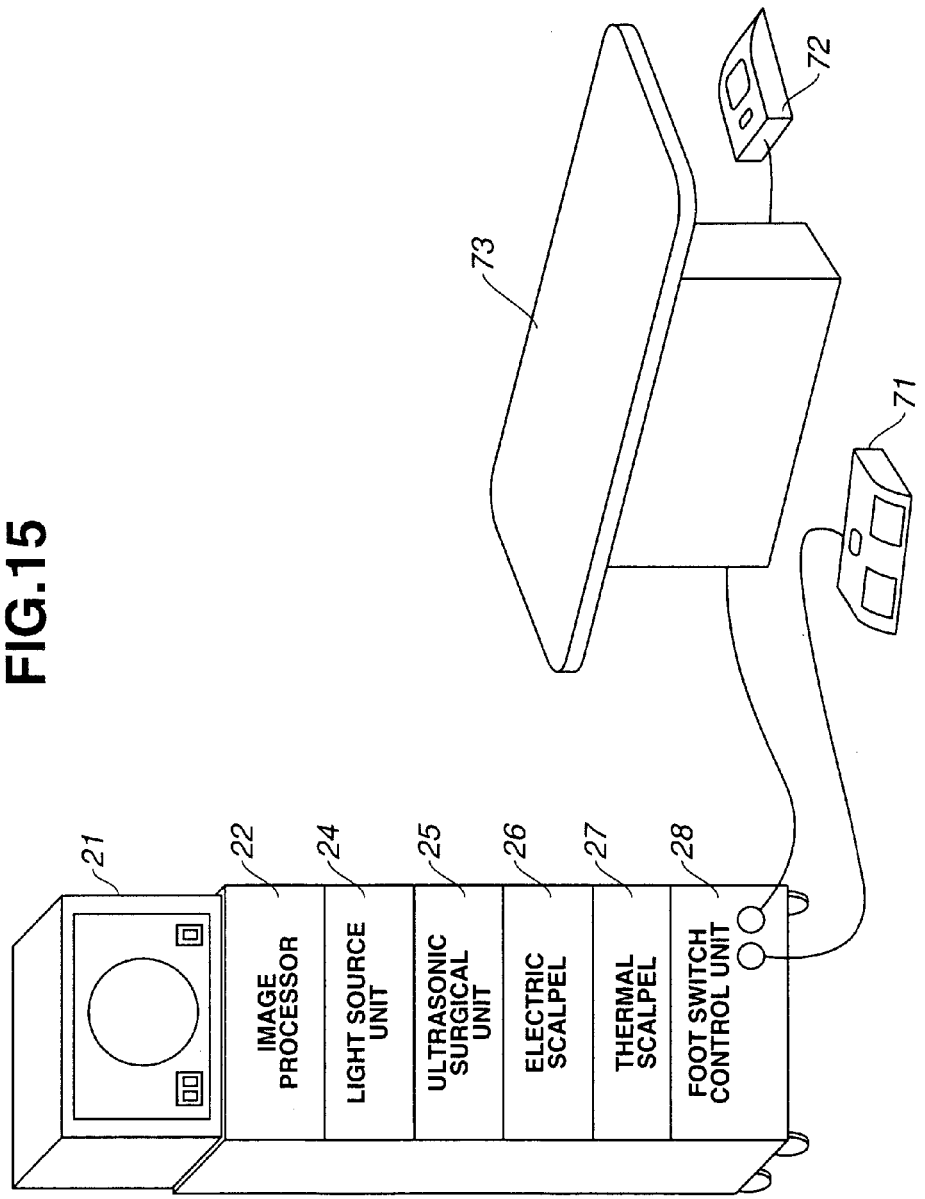
FIG. 15 to FIG. 19 relate to Embodiment 4 of the present invention.

As shown in FIG. 15, a foot switch 71 and a foot switch 72 are connected to the foot switch control device 28 of the present embodiment.

The foot switch 71 and foot switch 72 are composed of one or more functional switches and a selection switch. For example, it can be used by different surgeons at the left and right sides of the surgery stand 73. The foot switch 71 and foot switch 72 may be distinguished by providing the foot switches with ID or by the connector of the foot switch control device 28 to which they are connected.

Figure 16:
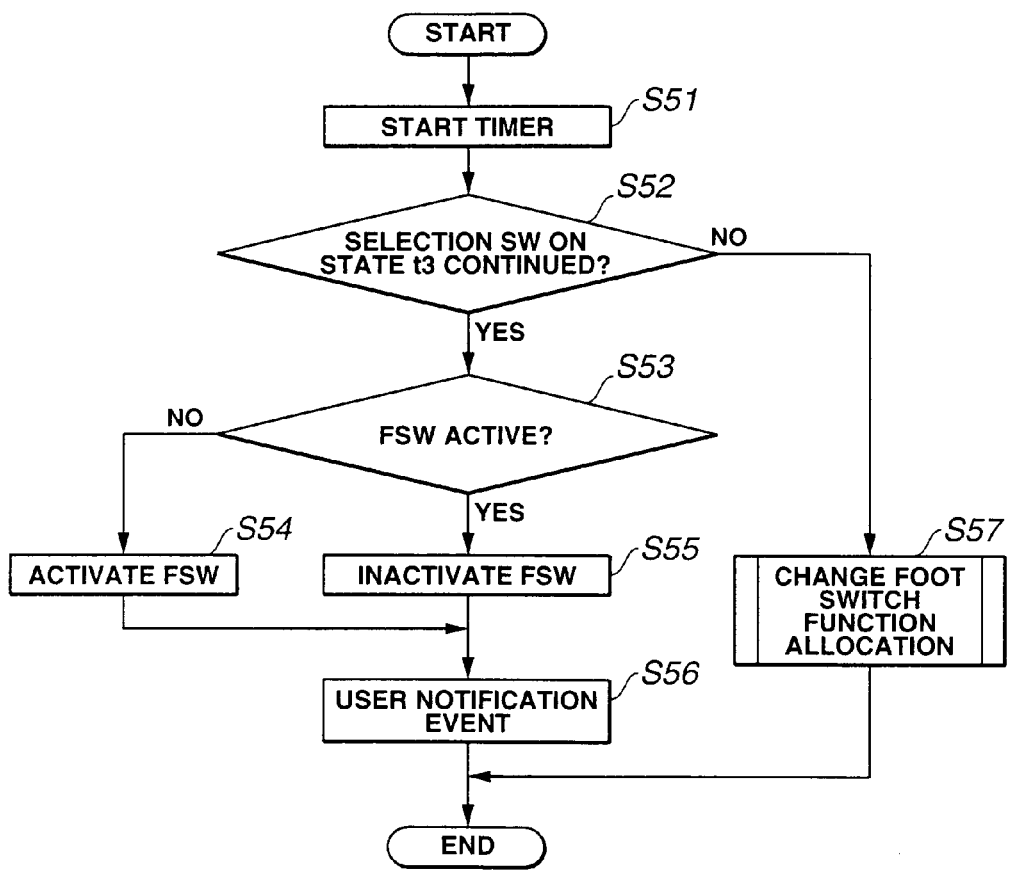
Figure 17:
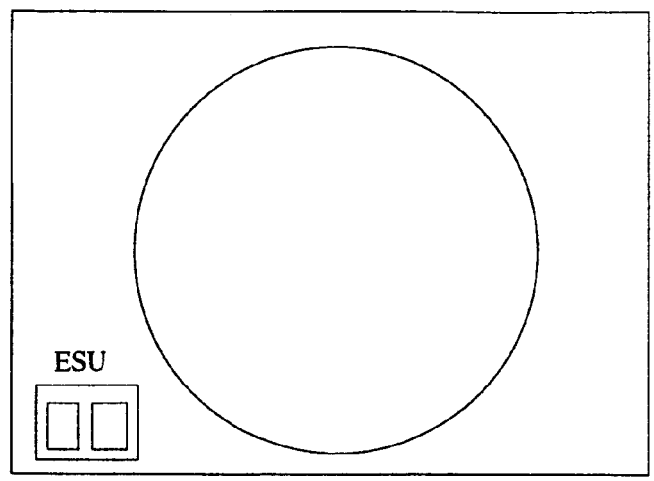
Figure 18:
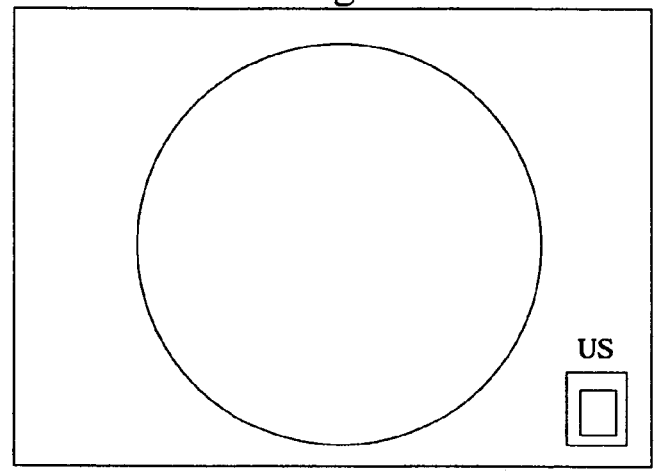
Figure 19:
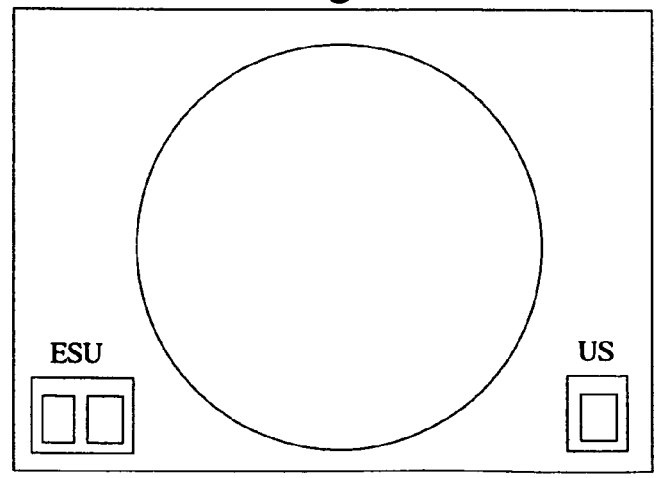
Figure 20:
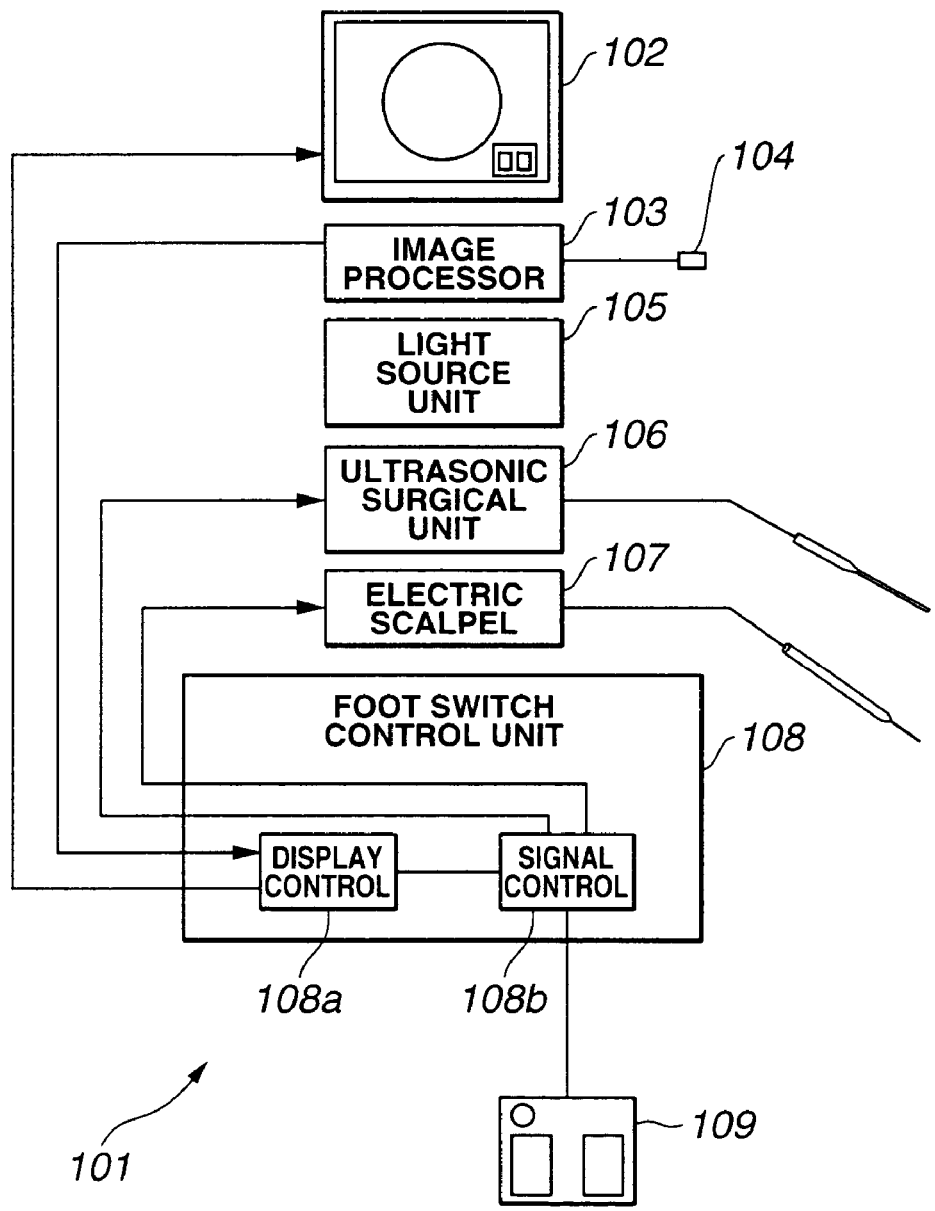
FIG. 20 to FIG. 23 relate to the conventional technology.

When the selection switch 29c is pushed within a prescribed time t3 or longer according to the flow chart shown in FIG. 16 (steps S51-S52), active and inactive modes of this switch are switched (steps S53-S55). When the active and inactive modes of the foot switch are switched, the display control unit 28a of the foot switch control device 28 notifies the user (user notification event), as shown in FIG. 17 to FIG. 19, that the active and inactive modes of the foot switch have been changed by the alteration of the foot switch state display of the presently active foot switch which is outputted in superposition on the endoscopic image or by notification by a voice output, notification by displaying on a panel of the foot switch control device 28, or combination of the notification methods (step S56).

Further, when the selection switch 29c has been pushed only for a prescribed time t3 or less, then the process of reallocating the switch functions allocated to the foot switches is carried out (step S57).

When the inactivated foot switch is stepped on, the foot switch control device 28 outputs no foot switch signal to the medical device. Furthermore, the user is notified, for example, by a voice signal, that the inactive foot switch is stepped on.

With the present embodiment, one or more than one surgeon can simultaneously conduct surgery by using a plurality of foot switches. Moreover, because the foot switches which are not used are inactivated, the probability of producing an output erroneously is decreased and the convenience of the unit in use is increased.

Having described the preferred embodiments of the invention referring to the accompanying drawings, it should be understood that the present invention is not limited to the those precise embodiments and various changes and modifications thereof could be made by one skilled in the art without departing from the spirit or scope of the invention as defined in the appended claims.

What is claimed is:

1. A switch control apparatus comprising:
    an image reception unit for receiving an image signal from an image pickup device for picking up the image of an object;
    a medical instrument;
    an operation switch for operating the medical instrument;
    a selection switch for changing the allocation state of the medical instrument and the operation switch;
    a changing-over signal reception unit for receiving a changing-over signal from the selection switch;
    an image synthesis unit for synthesizing an image signal for displaying, in the image reception unit, the object image based on the image signal superimposed with information relating to the operation switch based on the changing-over signal received by the changing-over signal reception unit;
    a display toggle switch for turning on or off the superimposing of information related to the operation switch displayed in the image reception unit; and
    a synthesis cancellation unit for canceling the synthesis processing of the image synthesis unit after the changing-over signal has been received and a prescribed time has elapsed.

2. The switch control apparatus according to claim 1, further comprising:
    an elapsed time measurement unit which starts measuring an elapsed time after the changing-over signal has been received;
    an elapsed time judgment unit for judging whether the operation signal from the operation switch has been received while the elapsed time is within the prescribed time; and
    an operation allocation cancellation unit for returning the allocation state of the operation switch to a prescribed state when the elapsed time judgment unit has judged that the elapsed time exceeds the prescribed time.

3. The switch control apparatus according to claim 2, further comprising:
    a resynthesizing unit for resynthesizing an image signal for displaying the object image superimposed on the information relating to the operation switch when the elapsed time judgment unit has judged that the prescribed time has elapsed and an operation signal has been received from the operation switch.

4. The switch control apparatus according to claim 3, wherein:
    the changing-over signal comprises a signal for switching between the active and inactive modes of operation of the operation switch, and
    the resynthesizing unit synthesizes an image signal for displaying the object image superimposed on the information indicating that the operation switch is inactive when an operation signal has been received from the operation switch set to the inactive mode.

5. The switch control apparatus according to claim 2, wherein the operation switch and the selection switch are provided in a foot switch.

6. The switch control apparatus according to claim 1, wherein:
    the changing-over signal comprises a signal for switching between the active and inactive modes of operation of the operation switch; and
    the image synthesis unit synthesizes an image signal for displaying the object image superimposed on the information indicating that the operation switch is inactive when an operation signal has been received from the operation switch set to the inactive mode.

7. The switch control apparatus according to claim 6, wherein the operation switch and the selection switch are provided in a foot switch.

8. The switch control apparatus according to claim 1, wherein the operation switch and the selection switch are provided in a foot switch.

9. A switch control method comprising:
    an image reception step of receiving an image signal from an image pickup device for picking up the image of an object;
    a changing-over step for changing the allocation state of a medical instrument and an operation switch for operating the medical instrument;
    an image synthesis step of generating a synthesized image by superimposing the object image based on the image signal on the information relating to the operation switch based on the changing-over signal from the changing-over step;

a display control step of turning on or off the superimposing of information related to the operation switch; and a synthesis cancellation step of canceling the synthesis processing of the image synthesis step after the changing-over signal has been received and a prescribed time has elapsed.

10. The switch control method according to claim 9, further comprising:

an elapsed time measurement step of starting the measurement of an elapsed time after the changing-over signal has been received;

an elapsed time judgment step of judging whether the operation signal from the operation switch has been received while the elapsed time is within the prescribed time; and an operation allocation cancellation step of returning the allocation state of the operation switch to a prescribed state when it is judged that the elapsed time exceeds the prescribed time; in the elapsed time judgment step.

11. The switch control method according to claim 10, further comprising:

a resynthesizing step of resynthesizing an image signal for superimposing the object image on information relating to the operation switch when it is judged that the prescribed time has elapsed in the elapsed time judgment step and an operation signal has been received from the operation switch.

12. The switch control method according to claim 11, wherein:

the changing-over signal comprises a signal for switching between the active and inactive modes of operation of the operation switch, and the resynthesizing step synthesizes an image signal in which the object image is superimposed on the information indicating that the operation switch is inactive when an operation signal has been received from the operation switch set to the inactive mode.

13. The switch control method according to claim 9, wherein:

the changing-over signal comprises a signal for switching between the active and inactive modes of operation of the operation switch, and the image synthesis step synthesizes an image signal in which the object image is superimposed on the information indicating that the operation switch is inactive when an operation signal has been received from the operation switch set to the inactive mode.

* * * * *